(12) United States Patent
Alajmi et al.

(10) Patent No.: US 10,980,843 B1
(45) Date of Patent: Apr. 20, 2021

(54) BEE VENOM NANOPARTICLES

(71) Applicant: KING SAUD UNIVERSITY, Riyadh (SA)

(72) Inventors: Reem Atta Alajmi, Riyadh (SA); Nadin Mohamed Moubayed, Riyadh (SA); Manal Ahmed Gasmelseed Awad, Riyadh (SA); Hany Mohamed Yehia, Riyadh (SA); Manal Fawzy Elkhadragy, Riyadh (SA); Ibrahim Abdullah Barakat, Riyadh (SA); Faten Nasser Alsaqabi, Riyadh (SA); Amany Zein Elabedein Mahmoud Elshahidy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/801,086

(22) Filed: Feb. 25, 2020

(51) Int. Cl.
   *A61K 35/64* (2015.01)
   *A61K 9/51* (2006.01)
   *A61P 31/04* (2006.01)

(52) U.S. Cl.
   CPC ............... *A61K 35/64* (2013.01); *A61K 9/51* (2013.01); *A61P 31/04* (2018.01)

(58) Field of Classification Search
   CPC .................................. A61K 35/64; A61K 9/51
   See application file for complete search history.

(56) References Cited

U.S. PATENT DOCUMENTS

2012/0128784 A1   5/2012   Han et al.

FOREIGN PATENT DOCUMENTS

| CN | 109692326 A | 4/2019 |
|----|---|---|
| KR | 20100055025 A | 5/2010 |
| KR | 101667544 B1 * | 10/2016 |
| KR | 20190090910 A | 8/2019 |

OTHER PUBLICATIONS

Eze, Obioma B. L. et al., "Therapeutic Effect of Honey Bee Venom," Journal of Pharmaceutical, Chemical and Biological Sciences, Mar.-May 2016; 4(1):48-53.

Fennell, Jean F. et al., "Antibacterial Action of Melittin, a Polypeptide from Bee Venom," Proc. Soc. Exp. Biol. Med., 127(3): pp. 707-710 (1968).

Hegazi, Ahmed G. et al., "Antibacterial Activity of Bee Venom Collected from Apis mellifera Carniolan Pure and Hybrid Races by Two Collection Methods," Int. J. Curr. Microbiol. App. Sci., 4(4): pp. 141-149 (2015).

Zolfagharian, Hossein et al., "Bee Venom (*Apis mellifera*) an Effective Potential Alternative to Gentamicin for Specific Bacteria Strins," J. of Pharmacopuncture, 19(3): pp. 225-230 (2016).

* cited by examiner

*Primary Examiner* — Amy L Clark
(74) *Attorney, Agent, or Firm* — Nath, Goldberg & Meyer; Richard C. Litman

(57) ABSTRACT

Bee venom nanoparticles and methods of synthesizing bee venom nanoparticles are provided. The bee venom nanoparticles may be synthesized by drying bee venom, suspending the dried bee venom in a solvent to form a first bee venom solution, spraying the first bee venom solution into boiling water under ultrasonic conditions to form a bee venom solution including the bee venom nanoparticles, stirring the bee venom solution including the bee venom nanoparticles, and freeze-drying the bee venom solution. The resulting nanoparticles may be used in pharmaceutical compositions, and may be useful for their antimicrobial activities.

9 Claims, 7 Drawing Sheets

BEE VENOM NANOPARTICLES

BACKGROUND

1. Field

The disclosure of the present patent application relates to nanotechnology, and particularly to bee venom nanoparticles, methods of synthesizing bee venom nanoparticles, and the use of bee venom nanoparticles as antimicrobial agents.

2. Description of the Related Art

Recently, nanoparticles have demonstrated important uses in a variety of fields. Nanoparticles have been used in a vast array of applications, including electronics, sensing, optics, and medicine.

Synthesis of nanoparticles has been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce by-products that pose increased risks to human health and the environment.

In recent years, green or environmentally friendly chemical methods have been developed to prepare nanoparticles using plant extracts. Green chemistry has the advantage of being fast, environmentally friendly, and economical. However, the rise of green methods of preparing nanoparticles has also demonstrated that the activities and characteristics of the nanoparticles vary significantly, depending upon the detailed method of synthesis and specific plant extract used.

Bee venom, and particularly honey bee venom and wasp venom, have been shown to contain a variety of biologically active proteins, including toxins. For this reason, bee venom has been studied in pharmacology, and considered as a potential drug design template.

Thus, bee venom nanoparticles, methods of synthesizing bee venom nanoparticles, and methods of using bee venom nanoparticles as antimicrobial agents solving the aforementioned problems are desired.

SUMMARY

The bee venom nanoparticles may be synthesized by harvesting bee venom, drying the bee venom, suspending the dried bee venom in a solvent to form a first bee venom solution, spraying the first bee venom solution into boiling water under ultrasonic conditions to form a bee venom solution with bee venom nanoparticles, stirring the bee venom solution with bee venom nanoparticles, and freeze-drying the bee venom solution with bee venom nanoparticles. The drying step may include air-drying the bee venom. The solvent may be any suitable solvent, including but not limited to methanol. In an embodiment, the dried bee venom may be suspended in a solvent at a ratio of 5 mg venom per 1 ml solvent. The spraying step may include spraying the first bee venom solution dropwise into 50 ml boiling water at a flow rate of 0.2 ml/min. The stirring step may include stirring the bee venom solution with bee venom nanoparticles at 600 rpm.

An embodiment of the present subject matter is directed to a pharmaceutical composition including the bee venom nanoparticles and a pharmaceutically acceptable carrier.

An embodiment of the present subject matter is directed to a method of making a pharmaceutical composition including mixing the bee venom nanoparticles under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of inhibiting microbial growth, including administering to a subject in need thereof a therapeutically effective amount of a pharmaceutical composition according to the present subject matter.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
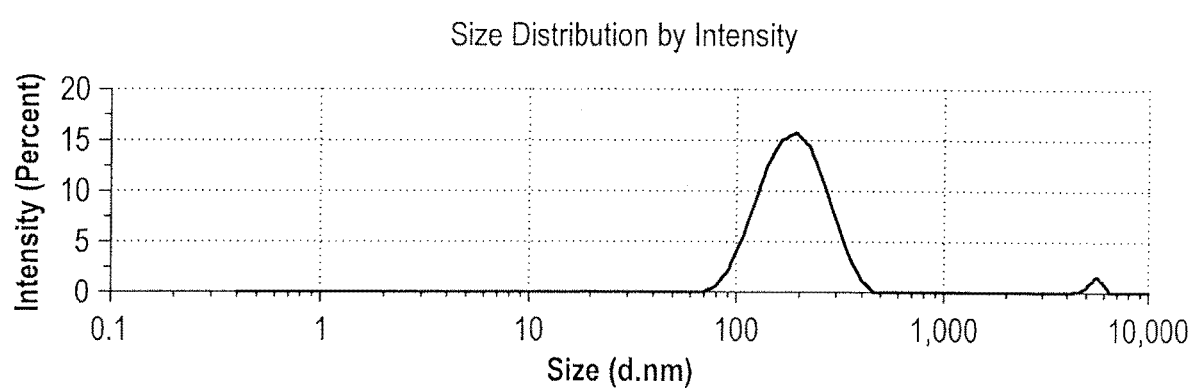
FIG. 1 depicts a zetasizer spectrum of the bee venom nanoparticles.
Figure 2A:
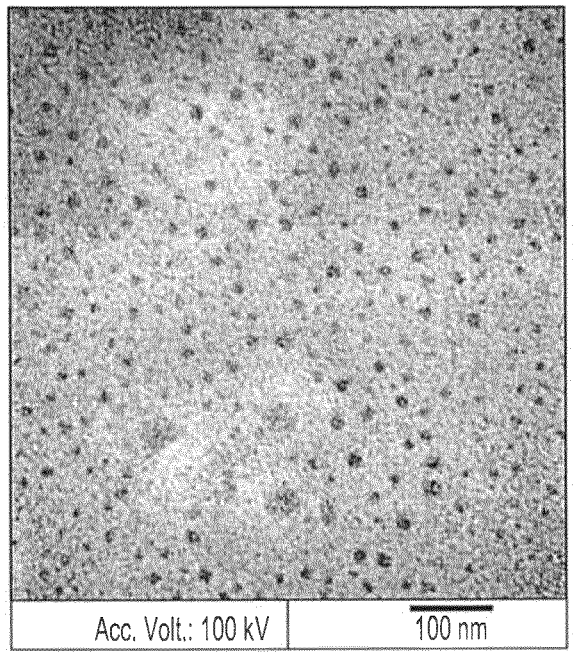
FIG. 2A depicts a transmission electron micrograph of the bee venom nanoparticles.
Figure 2B:
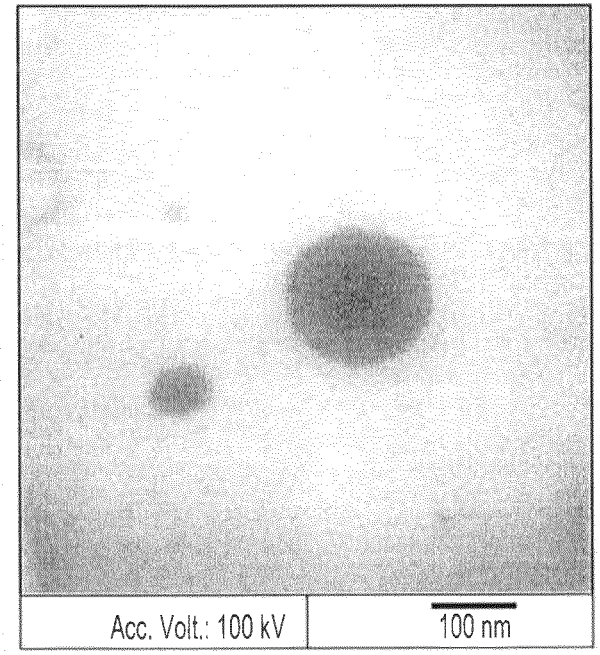
FIG. 2B depicts a transmission electron micrograph of the bee venom nanoparticles.
Figure 2C:
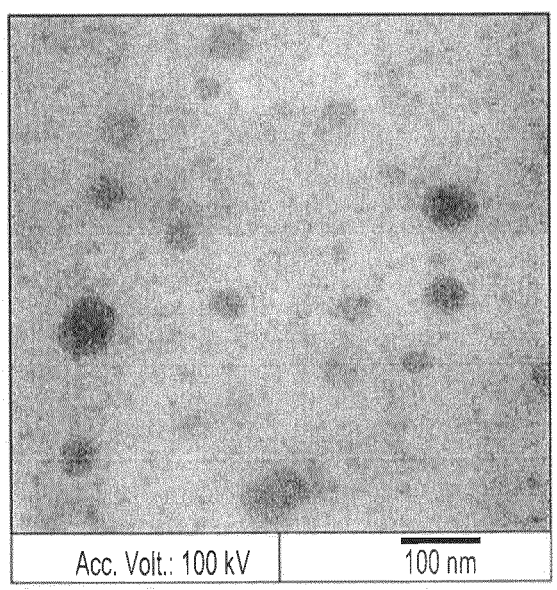
FIG. 2C depicts a transmission electron micrograph of the bee venom nanoparticles.
Figure 2D:
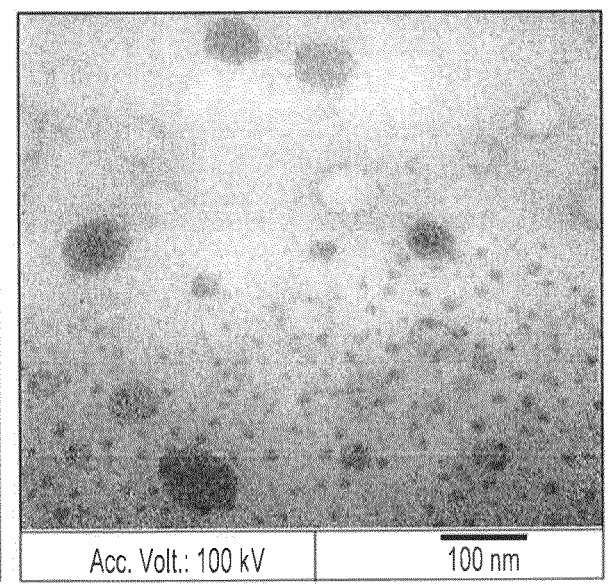
FIG. 2D depicts a transmission electron micrograph of the bee venom nanoparticles.

The bee venom nanoparticles may be synthesized by harvesting bee venom, drying the bee venom, suspending the dried bee venom in a solvent to form a first bee venom solution, spraying the first bee venom solution into boiling water under ultrasonic conditions to form a bee venom solution with bee venom nanoparticles, stirring the bee venom solution with bee venom nanoparticles, and freeze-drying the bee venom solution with bee venom nanoparticles. The drying step may include air-drying the bee venom. The solvent may be any suitable solvent, including but not limited to methanol. In an embodiment, the dried bee venom may be suspended in a solvent at a ratio of 5 mg dried bee venom per 1 ml solvent. The spraying step may include spraying the first bee venom solution dropwise into 50 ml boiling water at a flow rate of 0.2 ml/min. The stirring step may include stirring the bee venom solution with bee venom nanoparticles at 600 rpm.

In an embodiment, the bee venom may be harvested from one or more species of honey bees. In a further embodiment, the honey bees may be of the species *Apis cerana*.

In an embodiment, the bee venom nanoparticles may have an average particle diameter of about 171.3 nm with a polydispersity of about 0.493.

As used herein, the term "about," when used to modify a numerical value, means within ten percent of that numerical value.

An embodiment of the present subject matter is directed to a pharmaceutical composition comprising the bee venom nanoparticles and a pharmaceutically acceptable carrier.

An embodiment of the present subject matter is directed to a method of making a pharmaceutical composition including mixing the bee venom nanoparticles with a pharmaceutically acceptable carrier. For example, the method od making a pharmaceutical composition can include mixing the bee venom nanoparticles under sterile conditions with a pharmaceutically acceptable carrier with preservatives, buffers, and/or propellants to create the pharmaceutical composition.

An embodiment of the present subject matter is directed to a pharmaceutical composition including the bee venom nanoparticles. To prepare the pharmaceutical composition, the bee venom nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The bee venom nanoparticles can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the bee venom nanoparticles or an amount effective to treat a disease, such as a bacterial infection, may be determined initially from the Examples described herein and adjusted for specific targeted diseases using routine methods.

The bee venom nanoparticles can be administered to a subject in need thereof. In an embodiment, the bee venom nanoparticles can be administered to a subject in need thereof to inhibit microbial growth and/or prevent or treat a microbial infection. In a further non-limiting embodiment, the microbe can be a gram-positive bacterium, a gram-negative bacterium, or a fungus. The microbe may be a microbe selected from the group consisting of *Pseudomonas aeruginosa*, *Candida albicans*, *Salmonella enterica*, *Escherichia coli*, and *Staphylococcus aureus*.

An embodiment of the present subject matter is directed to a method of preventing microbial growth, comprising administering to a subject in need thereof a therapeutically effective amount of the pharmaceutical composition according to the present subject matter.

The bee venom nanoparticles or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrastemal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The following examples illustrate the present subject matter.

EXAMPLE 1

Synthesis of Bee Venom Nanoparticles

Bee venom from *Apis cerana* was collected during daylight hours using an electric venom collector (Bee Venom Collector—SMART BEE+3 panels, Serbia). The venom was dried in the open air, and the resulting dried bee venom (hereinafter crude bee venom), which appeared as a white crystalline substance, was stored at 4° C. in dark glass bottles and protected from exposure to direct sunlight. The dried bee venom was then dissolved in methanol at a concentration of 5 mg/ml, and this solution was sprayed into boiling water (50 ml) drop-wise with a flow rate of 0.2 m/min under ultrasonic conditions. After sonication, the resulting solution was stirred at 600 rpm and freeze-dried.

EXAMPLE 2

Characterizing the Bee Venom Nanoparticles

Bee venom nanoparticles synthesized according to Example 1 were analyzed using dynamic light scattering (DLS). The Z-average mean diameter (d.nm) was found to be 171.3 and the polydispersity index (Pdl) of the bee venom nanoparticles was 0.493 (See Table 1 and FIG. 1)

TABLE 1

Zetasizer Measurement of Bee Venom Nanoparticles

|  |  |  | Size (d.nm) | % Intensity | St Dev (d.nm) |
|---|---|---|---|---|---|
| Z-Average (d. nm) | 171.3 | Peak 1 | 195.7 | 98.2 | 65.62 |
| PDI | 0.493 | Peak 2 | 5455 | 1.8 | 261.6 |
| Intercept | 0.906 | Peak 3 | 0.000 | 0.0 | 0.000 |

Transmission electron microscopy (TEM) was used to identify the size, shape, and morphology of the bee venom nanoparticles (See FIGS. 2A-2D). The bee venom nanoparticles examined by TEM were well dispersed and mostly spherical in shape.

EXAMPLE 3

Antibacterial Activity of Bee Venom Nanoparticles

Bacterial and yeast strains tested include *Pseudomonas aeruginosa* ATCC 27853, *Salmonella enterica* LT2, *Escherichia coli* ATCC 25966, *Staphylococcus aureus* ATCC 25923, and *Candida albicans* ATCC 10231. Muller Hinton broth medium was placed into test tubes (10 ml per tube) and autoclaved at 121° C. for 15-20 minutes. Active bacterial cultures of each strain to be tested were inoculated in the prepared test tubes at 37° C. for 24 hours until they reached a turbidity of 0.1 on the McFarland scale (0.5-0.1). Optical density was measured using a spectrophotometer (Biochrom Ltd. Cambridge CB4 0FJ England) at a wavelength of 600 nm.

Microplates of crude bee venom and bee venom nanoparticles were prepared by first dissolving 0.1 mg of crude bee venom or of bee venom nanoparticles (prepared according to Example 1) in 2 ml saline solution (0.85% NaCl) to form crude bee venom solution and bee venom nanoparticle solution. These solutions were then sterilized using Millipore 0.2 μm filters and serially diluted to form 50%, 25%, 12.5%, 6.25%, 3.125%, and 1.562% dilutions, respectively. Then 100 μl of each dilution were added to individual wells of the microtiter plate and the microtiter plates were incubated at 37° C. for 24 hours. The absorbance (OD) was then read at 450 nm for each well and the absorbance of the wells treated with crude bee venom was compared to the absorbance of the wells treated with bee venom nanoparticles. These results are displayed in FIGS. 3A-3E.

Figure 3A:
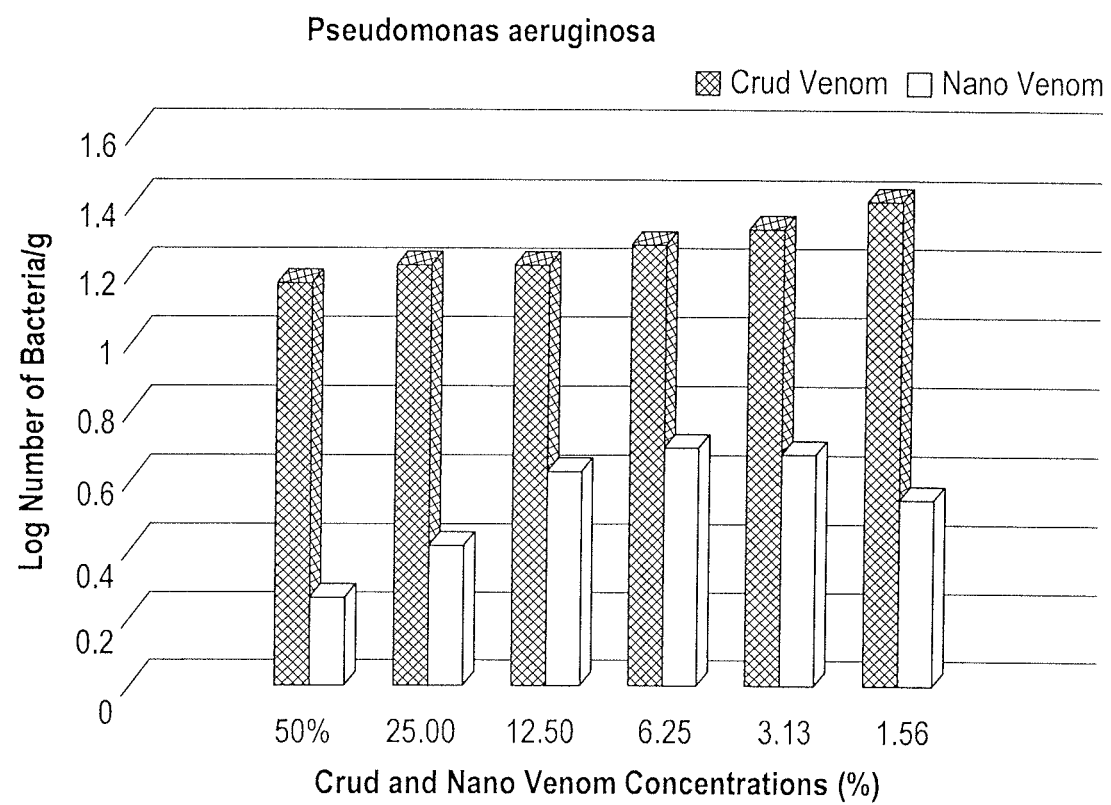
FIG. 3A depicts a graph of the inhibitory effect of the bee venom nanoparticles on the growth of *Pseudomonas aeruginosa*.

As illustrated in FIG. 3A, the growth rate (log number of bacteria per gram) of *P. aeruginosa* was reduced more by treatment with bee venom nanoparticles than by treatment with crude bee venom. At the 50% dilution, the inhibition ratio of bee venom nanoparticles compared to crude bee venom was 78.59%. This inhibition was concentration dependent, and increasing dilution of the bee venom nanoparticles/crude bee venom resulted in a respective increase in the *P. aeruginosa* growth rate.

Figure 3B:
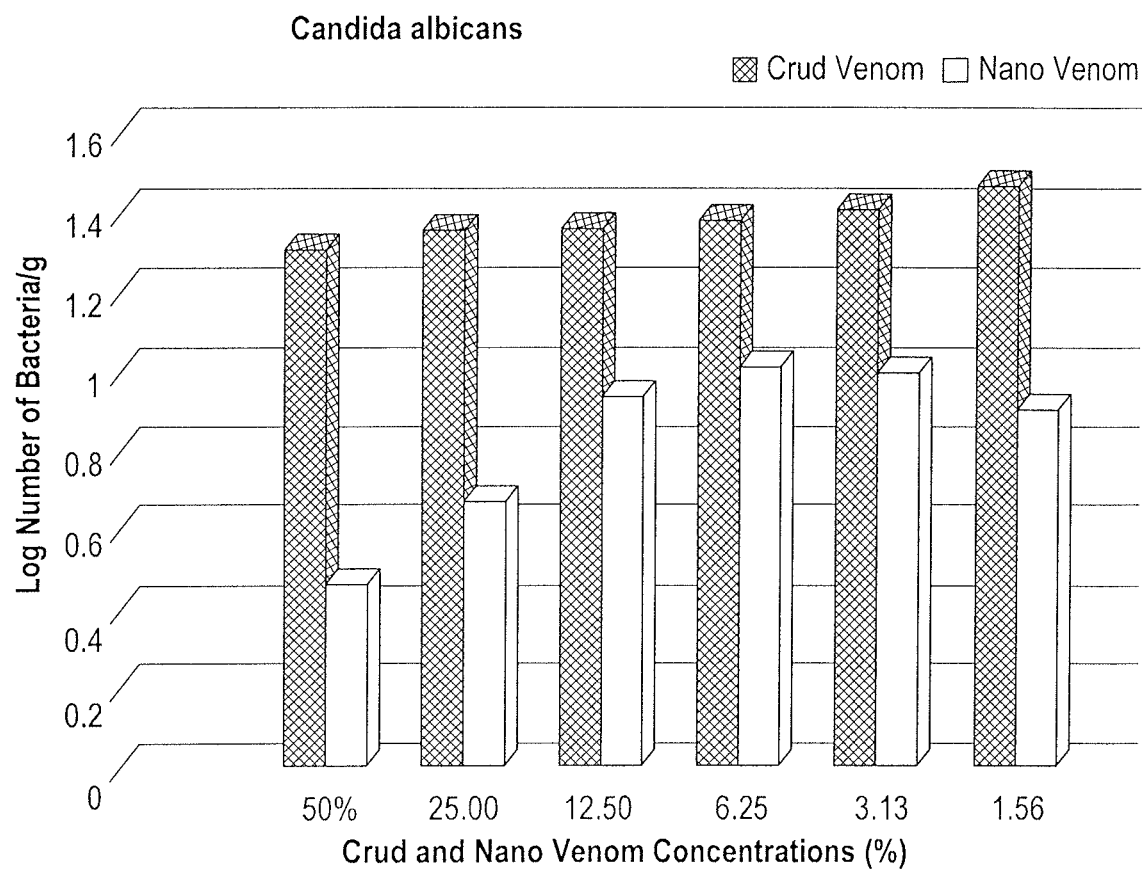
FIG. 3B depicts a graph of the inhibitory effect of the bee venom nanoparticles on the growth of *Candida albicans*.

As illustrated in FIG. 3B, the growth rate (log number of bacteria per gram) of *C. albicans* was reduced more by treatment with bee venom nanoparticles than the treatment with crude bee venom. At the 50% dilution, the inhibition ratio of bee venom nanoparticles compared to crude bee venom was 64.38%. This inhibition was concentration dependent, and increasing dilution of the bee venom nanoparticles/crude bee venom resulted in a respective increase in the *C. albicans* growth rate.

Figure 3C:
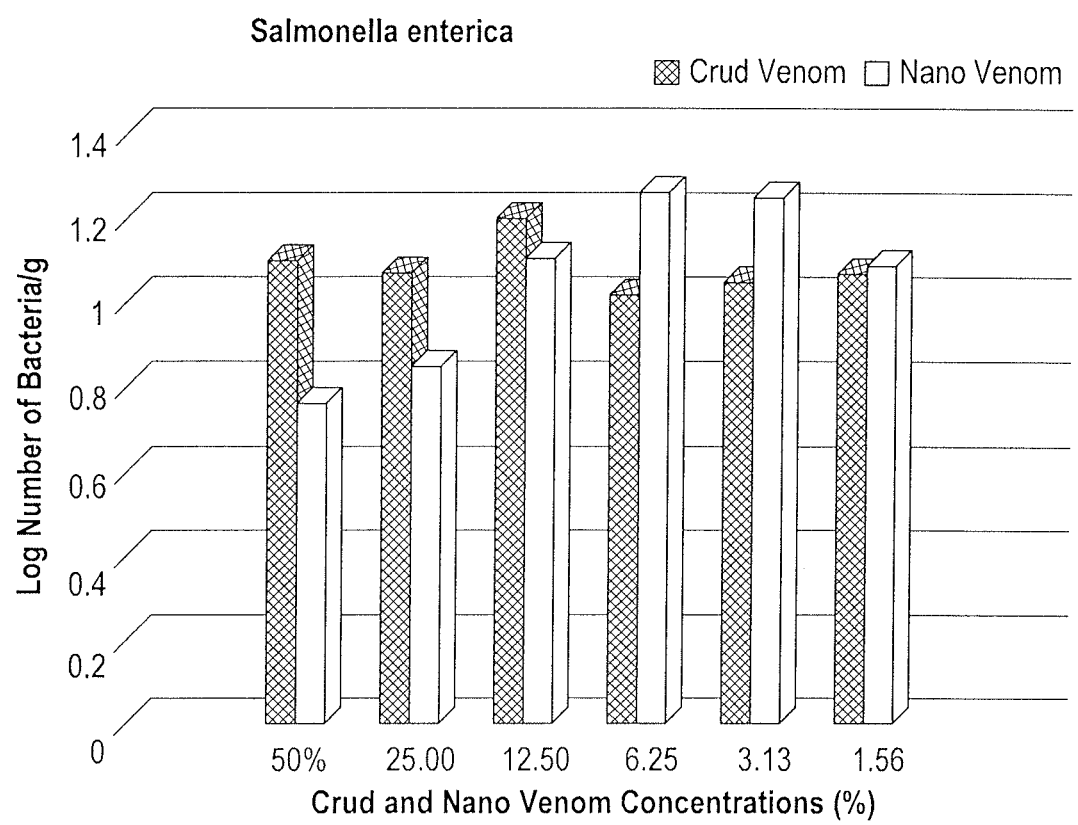
FIG. 3C depicts a graph of the inhibitory effect of the bee venom nanoparticles on the growth of *Salmonella enterica*.

As illustrated in FIG. 3C, the growth rate (log number of bacteria per gram) of *S. enterica* was reduced more by treatment with bee venom nanoparticles than the treatment with crude bee venom. At the 50% dilution, the inhibition ratio of bee venom nanoparticles compared to crude bee venom was 30%. This inhibition was concentration dependent, and increasing dilution of the bee venom nanoparticles/crude bee venom resulted in a respective increase in the *S. enterica* growth rate. At the lower concentrations (dilution factor of 6.25% and below) the inhibition ratio of bee venom nanoparticles compared to crude bee venom was almost equivalent.

Figure 3D:
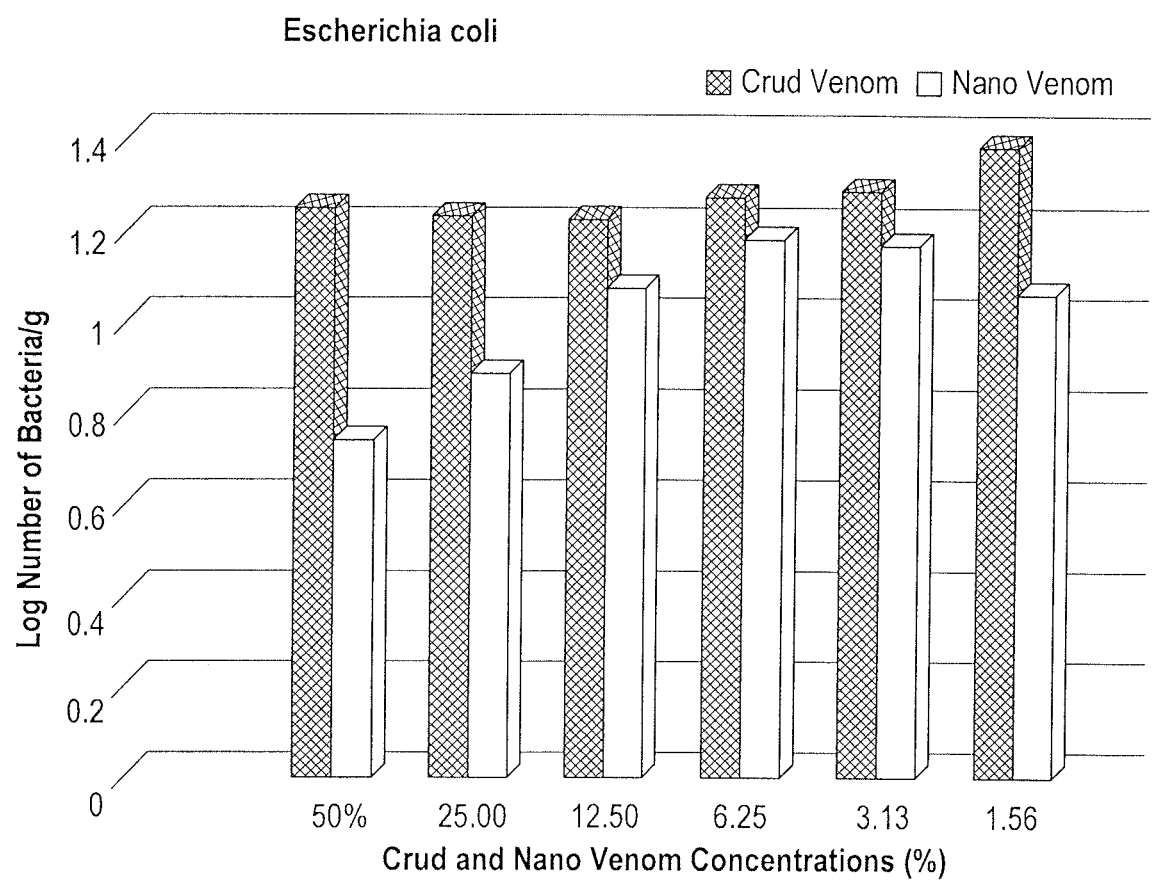
FIG. 3D depicts a graph of the inhibitory effect of the bee venom nanoparticles on the growth of *Escherichia coli*.

As illustrated in FIG. 3D, the growth rate (log number of bacteria per gram) of *E. coli* was reduced more by treatment with bee venom nanoparticles than be treatment with crude bee venom. At the 50% dilution, the inhibition ratio of bee venom nanoparticles compared to crude bee venom was 40.88%. This inhibition was concentration dependent, and increasing dilution of the bee venom nanoparticles/crude bee venom resulted in a respective increase in the *E. coli* growth rate.

Figure 3E:
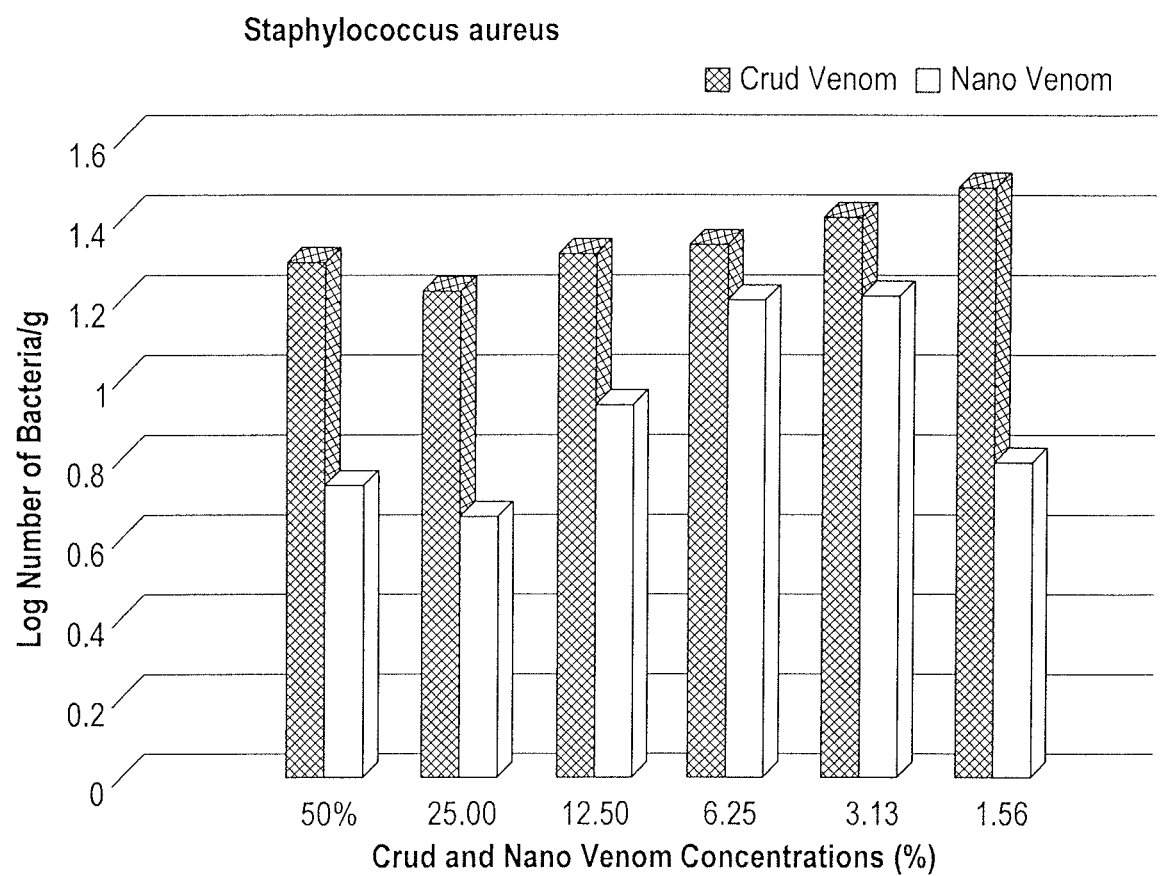
FIG. 3E depicts a graph of the inhibitory effect of the bee venom nanoparticles on the growth of *Staphylococcus aureus*.

As illustrated in FIG. 3E, the growth rate (log number of bacteria per gram) of *S. aureus* was reduced more by treatment with bee venom nanoparticles than the treatment with crude bee venom. At the 50% dilution, the inhibition ratio of bee venom nanoparticles compared to crude bee venom was 49.18%. This inhibition was concentration dependent, and increasing dilution of the bee venom nanoparticles/crude bee venom resulted in a respective increase in the *S. aureus* growth rate.

It is to be understood that the bee venom nanoparticles are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing bee venom nanoparticles, comprising:
   (a) harvesting bee venom;
   (b) drying bee venom;
   (c) suspending the dried bee venom in a solvent to form a first bee venom solution;
   (d) spraying the first bee venom solution into boiling water under ultrasonic conditions to form a bee venom solution, the bee venom solution containing bee venom nanoparticles;
   (e) stirring the bee venom solution containing bee venom nanoparticles; and
   (f) freeze-drying the bee venom solution containing bee venom nanoparticles.

2. The method of synthesizing bee venom nanoparticles as recited in claim 1, wherein the drying step comprises air-drying the bee venom.

3. The method of synthesizing bee venom nanoparticles as recited in claim 1, wherein the bee venom nanoparticles have an average particle diameter of 171.3 nm and a polydispersity of 0.493.

4. The method of synthesizing bee venom nanoparticles as recited in claim 1, wherein the harvesting step comprises harvesting bee venom from honey bees.

5. The method of synthesizing bee venom nanoparticle as recited in claim 4, wherein the honey bees are honey bees of the species *Apis cerana*.

6. The method of synthesizing bee venom nanoparticles as recited in claim 1, wherein the solvent comprises methanol.

7. The method of synthesizing bee venom nanoparticles as recited in claim 1, wherein the dried bee venom is suspended in solvent at a 5 mg:1 ml ratio.

8. The method of synthesizing bee venom nanoparticles as recited in claim 1, wherein the spraying step further comprises spraying the first bee venom solution dropwise into 50 ml boiling water at a flow rate of 0.2 ml/min.

9. The method of synthesizing bee venom nanoparticles as recited in claim 1, wherein the stirring step further comprises stirring the bee venom solution including the bee venom nanoparticles at 600 rpm.

* * * * *